United States Patent

Gerlach et al.

(10) Patent No.: US 6,936,631 B2
(45) Date of Patent: Aug. 30, 2005

(54) BICYCLIC IMIDAZO-5-YL-AMINE DERIVATIVES

(75) Inventors: Matthias Gerlach, Brachttal (DE); Corinna Maul, Aachen (DE)

(73) Assignee: Gruenenthal GmbH, Aachen (DE)

(*) Notice: Subject to any disclaimer, the term of this patent is extended or adjusted under 35 U.S.C. 154(b) by 150 days.

(21) Appl. No.: 10/633,579

(22) Filed: Aug. 5, 2003

(65) Prior Publication Data

US 2004/0023927 A1 Feb. 5, 2004

Related U.S. Application Data

(62) Division of application No. 10/117,335, filed on Apr. 8, 2002, now Pat. No. 6,657,064, which is a continuation of application No. PCT/EP00/09097, filed on Sep. 18, 2000.

(30) Foreign Application Priority Data

Oct. 8, 1999 (DE) .......................................... 199 48 434
Oct. 8, 1999 (DE) .......................................... 199 48 436

(51) Int. Cl.⁷ ...................... C07D 487/02; A61K 31/41
(52) U.S. Cl. .................... 514/383; 514/393; 548/262.4; 548/303.1
(58) Field of Search ................................. 514/383, 393; 548/262.4, 303.1, 266.2

(56) References Cited

U.S. PATENT DOCUMENTS 6,657,064 B2 * 12/2003 Gerlach et al. .......... 546/273.1

FOREIGN PATENT DOCUMENTS

EP 0518033 12/1992

OTHER PUBLICATIONS

Lantos et. al., "Novel Synthesis of Fused–Imidazoles III. Simplified Construction of the Imidazo[2,1–b]Thiazoline System", Heterocycles, vol. 24, No. 4, 1996.*

Ca 81:105382b, Cyclization of w–chLoro–w–acyLamido acetophenones, Drach et al., vol. 81, 1974.*

Ca 58:2443e, "Bicyclic heterocyclic componds with a common N atom amnoimidazo [2,1–b]tioazoles", Pyl et. al. See RN 95315–23–4 and 95315–26–7.*

Hugues Bienayme, et al. "A New Heterocyclic Multicomponent Reaction for the Combinatorial Synthesis of Fused 3–Aminoimidazoles" Angew. Chem. Int. Ed. vol. 37, No. 16, 1998, pp. 2234–2237.*

Katrin Groebke, et al., "Synthesis of Imidazo [1,2–a] annulated Pyridines, Pyrazines and Pyrimidines by a Novel Three–Component Condensation" Synlett, Jun. 1998.

Hugues Bienayme, et al., "A New Heterocyclic Multicomponent Reaction for the Combinatorial Synthesis of Fused 3–Aminoimidazoles" Angew. Chem. Int. Ed. vol. 37, No. 16, 1998.

* cited by examiner

Primary Examiner—Zinna Northington Davis
(74) Attorney, Agent, or Firm—Crowell & Moring LLP

(57) ABSTRACT

A novel bicyclic imidazo-5-yl-amine derivative of Formula I,

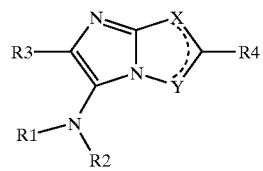

wherein X denotes $CR^5$, N or S, and Y in the case where X denotes S, denotes $CR^6$ or N and in all other cases denotes N, and methods for preparation thereof are disclosed. Also disclosed are methods for treating pain using the compound of Formula I, and pharmaceutical compositions comprising the compound of Formula I.

18 Claims, No Drawings

BICYCLIC IMIDAZO-5-YL-AMINE DERIVATIVES

CROSS REFERENCE TO RELATED APPLICATIONS

This application is a division of 10/117,335 filed Apr. 8, 2002 now U.S. Pat. No. 6,657,064

The present application is a continuation of international patent application No. PCT/EP00/09097, filed Sep. 18, 2000, designating the United States of America, the entire disclosure of which is incorporated herein by reference. Priority is claimed based on Federal Republic of Germany patent application Nos. 199 48 436.8, and 199 48 434.1, both filed Oct. 8, 1999.

BACKGROUND OF THE INVENTION

The present invention relates to substituted bicyclic imidazo-5-yl-amines and medicaments comprising these compounds.

Individual representatives from the class of bicyclic imidazo-5-yl-amines are described in EP-A-0 518 033. These compounds carry aromatic substituents bonded via a short alkyl bridge on the imidazole nitrogen which does not belong to the fused ring system. The compounds described in EP-A-0 518 033 as potent angiotensin antagonists which can be employed in medicaments for treatment of circulatory diseases such as high blood pressure.

Attempts have subsequently been made also to prepare those bicyclic imidazo-5-yl-amines which are not substituted on the imidazole nitrogen which does not belong to the fused ring system. However, these attempts had no (K. Groebke et al., Synlett 1998, 661) or only little success (H. Bienayme, K. Bouzid, Angew. Chem. 1998, 110 (16), 2349).

The present invention was therefore based on the object of providing bicyclic imidazo-5-yl-amines which are not substituted on the imidazole nitrogen which does not belong to the fused ring system, and medicaments comprising these compounds.

SUMMARY AND DETAILED DESCRIPTION OF THE INVENTION

The invention therefore provides bicyclic imidazo-5-yl-amines of the general formula I

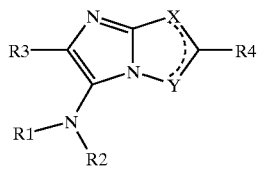

I wherein $R^1$ denotes $C(CH_3)_3$, $(CH_2)_6CN$, optionally substituted phenyl, $C_4$–$C_8$-cycloalkyl, $CH_2CH_2R$ (R=4-morpholino), 1,1,3,3-tetramethylbutyl or $CH_2R^a$, wherein $R^a$ represents hydrogen, $C_1$–$C_8$-alkyl (branched or unbranched), optionally substituted phenyl, CO(OR') (where R'=$C_1$–$C_8$-alkyl (branched or unbranched)), PO(OR")$_2$ (where R"=$C_1$–$C_4$-alkyl (branched or unbranched)) or Si($R^xR^yR^z$) (where $R^x$, $R^y$ and $R^z$ in each case independently of one another are $C_1$–$C_8$-alkyl (branched or unbranched), $C_4$–$C_8$-cycloalkyl or phenyl), $R^2$ denotes hydrogen; $COR^b$, wherein $R^b$ represents hydrogen, $C_1$–$C_8$-alkyl (branched or unbranched), $C_3$–$C_8$-cycloalkyl, $CH_2CH_2CO(OR')$ (where R'=$C_1$–$C_8$-alkyl (branched or unbranched)), adamantyl, optionally substituted phenyl, optionally substituted 1-naphthyl, 2-naphthyl, 2-pyridyl, 3-pyridyl, 4-pyridyl, thiazolyl or furoyl, $CH_2R^c$, wherein $R^c$ represents hydrogen, $C_1$–$C_8$-alkyl (branched or unbranched) or optionally substituted phenyl; $CH_2CH_2R^d$, wherein $R^d$ represents optionally substituted phenyl; or $CONHR^e$, wherein $R^e$ represents phenyl, $R^3$ denotes $C_1$–$C_8$-alkyl (branched or unbranched), $C_3$–$C_8$-cycloalkyl, optionally substituted phenyl, optionally substituted 1-naphthyl, 2-naphthyl, quinoline, anthracene, phenanthrene, benzothiophene, benzofurfuryl, optionally substituted pyrrole, 2-pyridyl, 3-pyridyl, 4-pyridyl, optionally substituted furfuryl or optionally substituted thiophene, X denotes $CR^5$, N or S, and Y, in the case where X denotes S, denotes $CR^6$ or N, and in all other cases denotes N, wherein the broken line in the structural element

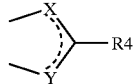

means that in the cases where X denotes S, Y is linked via a double bond with the C atom carrying $R^4$, and in all other cases one of the groups X or Y is linked via a double bond with the C atom carrying $R^4$ and the other particular group carries an additional hydrogen, $R^4$, $R^5$ and $R^6$ independently of one another denote hydrogen, $C_1$–$C_8$-alkyl (branched or unbranched); fluorine; chlorine; bromine; $CF_3$; CN; $NO_2$, $NHR^f$, wherein $R^f$ represents hydrogen, $C_1$–$C_8$-alkyl (branched or unbranched) or optionally substituted phenyl; $SR^g$, wherein $R^g$ represents hydrogen, $C_1$–$C_8$-alkyl (branched or unbranched), phenyl, pyridine, benzyl or fluorenyl; $OR^h$, wherein $R^h$ represents $C_1$–$C_8$-alkyl (branched or unbranched), optionally substituted phenyl or CO(OR') (R'=$C_1$–$C_8$-alkyl (branched or unbranched)); CO(OR') or $CH_2CO(OR')$, wherein R' in each case has the above-mentioned meaning or in the case of the group $CH_2CO(OR')$ also denotes hydrogen, or an optionally substituted phenyl group; and pharmaceutically acceptable salts thereof, excluding compounds in which either at the same time $R^1$ denotes $C(CH_3)_3$, $R^2$ denotes hydrogen, $R^3$ denotes unsubstituted phenyl, X denotes S and Y denotes N or $CR^6$, where $R^6$=hydrogen or $CH_2$—$CO_2$-ethyl, or at the same time $R^1$ denotes $C(CH_3)_3$, $R^2$ denotes hydrogen, $R^3$ denotes unsubstituted phenyl, Y denotes NH and X denotes N or $CR^5$, where $R^5$=$CO_2$ethyl.

Optionally substituted phenyl, optionally substituted 1-naphthyl, optionally substituted pyrrole, optionally substituted furfuryl, optionally substituted thiophene, optionally substituted isocyanate and optionally substituted alkyl, according to the instant invention, may be optionally substituted by one or more substituents selected from the group consisting of a halogen atom, cyano group, nitro group, carboxyl group, hydroxyl group, $C_1$–$C_4$ alkylamido group, $C_1$–$C_4$ alkylamino group, pyrrolidino group, branched or unbranched $C_1$–$C_6$ alkyl group, $C_1$–$C_4$ alkyl group substituted with one or more halogen atoms, $C_1$–$C_4$ alkoxy group, $C_1$–$C_4$ alkoxy group substituted with one or more halogen atoms, and halogen substituted phenoxy group.

Where $R^3$ is a substituted phenyl group, it is preferably 4-acetamidophenyl, 2-bromophenyl, 3-bromophenyl, 4-bromophenyl, 4-bromo-2-fluorophenyl, 5-bromo-2-fluorophenyl, 3-bromo-4-fluorophenyl, 4-tert-butylphenyl, 2-chloro-4-fluorophenyl, 2-chloro-6-fluorophenyl, 2-chlorophenyl, 3-chlorophenyl, 4-chlorophenyl, 4-cyanophenyl, 2,3-dichlorophenyl, 2,4-dichlorophenyl, 3,4-dichlorophenyl, 2,3-dimethoxyphenyl, 3,4-dimethoxyphenyl, 2,4-dimethylphenyl, 2,5-dimethylphenyl, 2-fluorophenyl, 3-fluorophenyl, 4-fluorophenyl, 4-hexylphenyl, 3-hydroxyphenyl, 2-methoxyphenyl, 2-methylphenyl, 3-methylphenyl, 4-methylphenyl, 4-nitrophenyl, 3-phenoxyphenyl, 4-(1-pyrrolidino)phenyl, 2-(trifluoromethyl)phenyl, 3-(trifluoromethyl)phenyl, 4-(trifluoromethyl)phenyl, 3,4,5-trimethoxyphenyl, 3-(4-chlorophenoxy)phenyl or 4-acetoxy-3-methoxyphenyl.

Where $R^3$ is a substituted 1-naphthyl group, it is preferably 4-dimethylaminonaphthyl, 2-ethoxynaphthyl or 4-methoxynaphthyl.

Where $R^3$ is a substituted pyrrole group, it is preferably 2-(1-(phenylsulfonyl)-pyrrole), 2-(N-methylpyrrole), 2-(N-(3,5-dichlorophenyl)-pyrrole or 2-(1-(4-chlorophenyl) pyrrole).

Where $R^3$ is a substituted furfuryl group, it is preferably 2-(5-acetoxymethylfurfuryl), 2-(5-methylfurfuryl), 2-(5-nitrofurfuryl), 2-[5-(3-nitrophenyl)furfuryl], 2-[5-(2-nitrophenyl)furfuryl], 2-(5-bromofurfuryl), 2-[5-(4-chlorophenyl)furfuryl], 2-(4,5-dimethylfurfuryl), 2-[5-(2-chlorophenyl)furfuryl], 2-(5-ethylfurfuryl) or 2-[5-(1,3-dioxalane)furfuryl].

Where $R^3$ is a substituted thiophene group, it is preferably 2-(5-chlorothiophenyl), 2-(5-methylthiophenyl), 2-(5-ethylthiophenyl), 2-(3-methylthiophenyl), 2-(4-bromothiophenyl), 2-(5-nitrothiophenyl), 5-(2-carboxythiophenyl), 2-[4-(phenylethyl)thiophenyl], 2-[5-(methylthio)thiophenyl], 2-(3-bromothiophenyl), 2-(3-phenoxythiophenyl) or 2-(5-bromothiophenyl).

Where $R^b$ is a substituted phenyl group, it is preferably 3,5-bis(trifluoromethyl)phenyl, 2-bromophenyl, 2-fluorophenyl, pentafluorophenyl, 2,4-difluorophenyl, 2,6-difluorophenyl, 2-chlorophenyl, 2,4-dichlorophenyl, 2-acetylphenyl, 2-methoxyphenyl, 2,6-dimethoxyphenyl, 2-(trifluoromethyl)phenyl, 2-methylphenyl, 3-bromophenyl, 3-fluorophenyl, 3-chlorophenyl, 3,4-dichlorophenyl, 3-methoxyphenyl, 3,4-dimethoxyphenyl, 3,4,5-trimethoxyphenyl, 3,5-dimethoxyphenyl, 3-(trifluoromethyl)phenyl, 3-methoxyphenyl, 4-bromophenyl, 4-fluorophenyl, 4-chlorophenyl, 4-methoxyphenyl, 4-(trifluoromethyl)phenyl, 4-tert-butylphenyl, 4-methylphenyl, 2-iodophenyl, 4-iodophenyl, 4-cyanophenyl, 2-nitrophenyl, 3-nitrophenyl, 3,5-dinitrophenyl, 4-nitrophenyl, 3,5-dichlorophenyl, 2,5-difluorophenyl, 2,4-dimethoxyphenyl, 3-nitro-4-methylphenyl, 2,5-dichlorophenyl, 2,3-difluorophenyl, 4-(trifluoromethoxy)phenyl, 2-(trifluoromethoxy)phenyl or 3-(trifluoromethoxy)phenyl.

Where $R^c$ is a substituted phenyl group, it is preferably 2-fluorophenyl, 2-chlorophenyl, 2-methylphenyl, 2-(trifluoromethyl)phenyl, 2-bromophenyl, 3-methoxyphenyl, 3-nitrophenyl, 3-chlorophenyl, 3-fluorophenyl, 3-phenoxyphenyl, 3-(trifluoromethoxy) phenyl, 3-bromophenyl, 3-chlorophenyl, 3-methylphenyl, 4-tert-butylphenyl, 4-fluorophenyl, 4-chlorophenyl, 4-vinylphenyl, 4-(trifluoromethoxy)phenyl, 3,5-dimethoxyphenyl, 3,5-difluorophenyl, 3,5-di (trifluoromethyl)phenyl, 3,5-difluorophenyl, 3,5-dimethylphenyl 2,3-dichlorophenyl, 2,3-dimethylphenyl, 2,3-difluorophenyl, 3-chloro-2-fluorophenyl, 2-chloro-4-fluorophenyl, 2,4-di(trifluoromethyl)phenyl, 2,4-dichlorophenyl, 2,4-difluorophenyl, 2,4-dimethylphenyl, 2,5-dichlorophenyl, 2,5-dimethylphenyl, 2,5-difluorophenyl, 3,4-dichlorophenyl, 3,4-difluorophenyl, 3,4-dimethylphenyl, 2,3,4-trifluorophenyl, 2,3,6-trifluorophenyl, 2,4,5-trifluorophenyl, 2,4,6-trimethylphenyl or pentafluorophenyl.

Where $R^d$ is a substituted phenyl group, it is preferably 3-chlorophenyl, 4-chlorophenyl, 4-carboxyphenyl, 4-acetylphenyl, 4-methoxyphenyl, 4-fluorophenyl, 4-nitrophenyl or 4-hydroxyphenyl.

Bicyclic imidazo-5-yl-amines which are particularly preferred according to the invention are tert-butyl-(5-furan-2-yl-imidazo[1,2-b][1,2,4]triazol-6-yl)-amine,
tert-butyl-(6-furan-2-yl-imidazo[2,1-b]thiazol-5-yl)-amine,
(5-tert-butylamino-6-furan-2-yl-imidazo[2,1-b]thiazol-3-yl)-acetic acid,
tert-butyl-(5-pyridin-2-yl-imidazo[1,2-b][1,2,4]triazol-6-yl)-amine,
tert-butyl-(6-pyridin-2-yl-imidazo[2,1-b]thiazol-5-yl)-amine,
tert-butyl-(5-pyridin-3-yl-imidazo[1,2-b][1,2,4]triazol-6-yl)-amine,
tert-butyl-(5-pyridin-4-yl-imidazo[1,2-b][1,2,4]triazol-6-yl)-amine,
tert-butyl-(6-cyclohexyl-imidazo[2,1-b]thiazol-5-yl)-amine,
tert-butyl-(5-methyl-imidazo[1,2-b][1,2,4]triazol-6-yl)-amine,
tert-butyl-(6-methyl-imidazo[2,1-b]thiazol-5-yl)-amine,
cyclohexyl-(5-pyridin-2-yl-imidazo[1,2-b][1,2,4]triazol-6-yl)-amine,
cyclohexyl-(6-pyridin-2-yl-imidazo[2,1-b]thiazol-5-yl)-amine,
(5-cyclohexylamino-6-pyridin-2-yl-imidazo[2,1-b]thiazol-3-yl)-acetic acid,
cyclohexyl-(6-pyridin-4-yl-imidazo[2,1-b]thiazol-5-yl)-amine,
cyclohexyl-(6-cyclohexyl-imidazo[2,1-b]thiazol-5-yl)-amine,
(6-cyclohexyl-5-cyclohexylamino-imidazo[2,1-b]thiazol-3-yl)-acetic acid,
(5-cyclohexylamino-6-methyl-imidazo[2,1-b]thiazol-3-yl)-acetic acid,
(2,6-dimethyl-phenyl)-(5-furan-2-yl-imidazo [1,2-b][1,2,4]triazol-6-yl)-amine,
(2,6-dimethyl-phenyl)-(6-pyridin-2-yl-imidazo[2,1-b]thiazol-5-yl)-amine,
(2,6-dimethyl-phenyl)-(6-pyridin-3-yl-imidazo[2,1-b]thiazol-5-yl)-amine,
(2,6-dimethyl-phenyl)-(6-pyridin-4-yl-imidazo[2,1-b]thiazol-5-yl)-amine,
methyl (6-cyclohexyl-imidazo[2,1-b]thiazol-5-ylamino)-acetate,
methyl (6-methyl-imidazo[2,1-b]thiazol-5-ylamino)-acetate,
tert-butyl-(2-phenyl-5H-imidazo[1,2-b]pyrazol-3-yl)-amine,
3-(5-tert-butylamino-imidazo[2,1-b]thiazol-6-yl)-phenol,
tert-butyl-[6-(3,4-dimethoxy-phenyl)-imidazo[2,1-b]thiazol-5-yl]-amine,
tert-butyl-[5-(2,3-dichloro-phenyl)-imidazo[1,2-b][1,2,4]triazol-6-yl]-amine,
tert-butyl-[6-(2,3-dichloro-phenyl)-imidazo[2,1-b]thiazol-5-yl]-amine,
tert-butyl-[5-(2,4-dichloro-phenyl)-imidazo[1,2-b][1,2,4]triazol-6-yl]-amine,
tert-butyl-[6-(2,4-dichloro-phenyl)-imidazo[2,1-b]thiazol-5-yl]-amine, tert-butyl-[5-(2-methoxy-phenyl)-imidazo[1,2-b][1,2,4] triazol-6-yl]-amine,
tert-butyl-[6-(2-methoxy-phenyl)-imidazo[2,1-b]thiazol-5-yl]-amine,
[5-tert-butylamino-6-(2-methoxy-phenyl)-imidazo[2,1-b] thiazol-3-yl]-acetic acid,
tert-butyl-(5-o-tolyl-imidazo[1,2-b][1,2,4]triazol-6-yl)-amine,
tert-butyl-(6-o-tolyl-imidazo[2,1-b]thiazol-5-yl)-amine,
tert-butyl-[5-(2,3-dimethoxy-phenyl)-imidazo[1,2-b][1,2,4] triazol-6-yl]-amine,
tert-butyl-[6-(2,3-dimethoxy-phenyl)-imidazo[2,1-b] thiazol-5-yl]-amine,
tert-butyl-(6-p-tolyl-imidazo[2,1-b]thiazol-5-yl)-amine,
(5-tert-butylamino-6-methyl-imidazo[2,1-b]thiazol-3-yl)-acetic acid,
N-tert-butyl-N-(6-phenyl-imidazo[2,1-b]thiazol-5-yl)-acetamide,
N-tert-butyl-N-(6-o-tolyl-imidazo[2,1-b]thiazol-5-yl)-acetamide,
butyl-[6-(4-tert-butyl-phenyl)-2-methyl-imidazo[2,1-b] thiazol-5-yl]amine,
tert-butyl-[5-(2-fluorophenyl)-imidazo[1,2-b][1,2,4]triazol-6-yl]-amine,
tert-butyl-[6-(2-fluorophenyl)-imidazo[2,1-b]thiazol-5-yl]-amine,
tert-butyl-(5-naphthaien-1-yl-imidazo[1,2-b][1,2,4]triazol-6-yl)-amine,
cyclohexyl-(5-naphthalen-1-yl-imidazo[1,2-b][1,2,4] triazol-6-yl)-amine,
[5-(2-bromophenyl)-imidazo[1,2-b][1,2,4]triazol-6-yl]-(1,1,3,3-tetramethyl-butyl)-amine,
N-[4-(6-cyclohexylamino-imidazo[1,2-b][1,2,4]triazol-5-yl)-phenyl]-acetamide,
tert-butyl-[5-(2,5-dimethyl-phenyl)-imidazo[1,2-b][1,2,4] triazol-6-yl]-amine,
cyclohexyl-[6-(2,4-dimethyl-phenyl)-imidazo[2,1-b] thiazol-5-yl]-amine,
cyclohexyl-[6-(2,5-dimethylphenyl)-imidazo[2,1-b]thiazol-5-yl]-amine,
N-tert-butyl-N-(6-p-tolyl-imidazo [2,1 -b]thiazol-5-yl)-acetamide,
[5-(2,4-dimethyl-phenyl)-imidazo[1,2-b][1,2,4]triazol-6-yl]-(1,1,3,3-tetramethyl-butyl)-amine,
[5-(2,5-dimethyl-phenyl)-imidazo[1,2-b][1,2,4]triazol-6-yl]-(1,1,3,3-tetramethyl-butyl)-amine,
N-butyl-N-[5-(2-chloro-6-fluorophenyl)-imidazo[1,2-b][1,2,4]triazol-6-yl]-acetamide or
N-butyl-N-[6-(4-tert-butyl-phenyl)-2-methyl-imidazo[2,1-b]thiazol-5-yl]-acetamide.

If the bicyclic imidazo-5-yl-amines according to the invention contain optically active carbon atoms, the present invention also provides the enantiomers of these compounds and mixtures thereof. The present invention also provides pharmaceutically acceptable salts thereof.

The invention furthermore provides medicaments or pharmaceutical compositions comprising as the active compound at least one bicyclic imidazo-5-yl-amine of the general formula I, in which $R^1$ to $R^6$, X and Y have the abovementioned meaning, in the form of the base or of pharmaceutically acceptable salts, preferably of hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid, or in particular of hydrochloric acid.

The medicaments according to the invention particularly preferably comprise as the active compound at least one bicyclic imidazo-5-yl-amine chosen from the group consisting of tert-butyl-(5-furan-2-yl-imidazo[1,2-b][1,2,4]triazol-6-yl)-amine,
tert-butyl-(6-furan-2-yl-imidazo[2,1-b]thiazol-5-yl)-amine,
(5-tert-butylamino-6-furan-2-yl-imidazo[2,1-b]thiazol-3-yl)-acetic acid,
tert-butyl-(5-pyridin-2-yl-imidazo[1,2-b][1,2,4]triazol-6-yl)-amine,
tert-butyl-(6-pyridin-2-yl-imidazo[2,1-b]thiazol-5-yl)-amine,
tert-butyl-(5-pyridin-3-yl-imidazo[1,2-b][1,2,4]triazol-6-yl)-amine,
tert-butyl-(5-pyridin-4-yl-imidazo[1,2-b][1,2,4]triazol-6-yl)-amine,
tert-butyl-(6-cyclohexyl-imidazo[2,1-b]thiazol-5-yl)-amine,
tert-butyl-(5-methyl-imidazo[1,2-b][1,2,4]triazol-6-yl)-amine,
tert-butyl-(6-methyl-imidazo[2,1-b]thiazol-5-yl)-amine,
cyclohexyl-(5-pyridin-2-yl-imidazo[1,2-b][1,2,4]triazol-6-yl)-amine,
cyclohexyl-(6-pyridin-2-yl-imidazo[2,1-b]thiazol-5-yl)-amine,
(5-cyclohexylamino-6-pyridin-2-yl-imidazo[2,1-b]thiazol-3-yl)-acetic acid,
cyclohexyl-(6-pyridin-4-yl-imidazo[2,1-b]thiazol-5-yl)-amine,
cyclohexyl-(6-cyclohexyl-imidazo[2,1-b]thiazol-5-yl)-amine,
(6-cyclohexyl-5-cyclohexylamino-imidazo[2,1-b]thiazol-3-yl)-acetic acid,
(5-cyclohexylamino-6-methyl-imidazo[2,1-b]thiazol-3-yl)-acetic acid,
(2,6-dimethyl-phenyl)-(5-furan-2-yl-imidazo[1,2-b][1,2,4] triazol-6-yl)-amine,
(2,6-dimethyl-phenyl)-(6-pyridin-2-yl-imidazo[2,1-b] thiazol-5-yl)-amine,
(2,6-dimethyl-phenyl)-(6-pyridin-3-yl-imidazo[2,1-b] thiazol-5-yl)-amine,
(2,6-dimethyl-phenyl)-(6-pyridin-4-yl-imidazo[2,1-b] thiazol-5-yl)-amine,
methyl (6-cyclohexyl-imidazo[2,1-b]thiazol-5-ylamino)-acetate,
methyl (6-methyl-imidazo[2,1-b]thiazol-5-ylamino)-acetate,
tert-butyl-(2-phenyl-5H-imidazo[1,2-b]pyrazol-3-yl)-amine,
3-(5-tert-butylamino-imidazo[2,1-b]thiazol-6-yl)-phenol,
tert-butyl-[6-(3,4-dimethoxy-phenyl)-imidazo[2,1-b] thiazol-5-yl]-amine,
tert-butyl-[5-(2,3-dichloro-phenyl)-imidazo[1,2-b][1,2,4] triazol-6-yl]-amine,
tert-butyl-[6-(2,3-dichloro-phenyl)-imidazo[2,1-b]thiazol-5-yl]-amine,
tert-butyl-[5-(2,4-dichloro-phenyl)-imidazo[1,2-b][1,2,4] triazol-6-yl]-amine,
tert-butyl-[6-(2,4-dichloro-phenyl)-imidazo[2,1-b]thiazol-5-yl]-amine,
tert-butyl-[5-(2-methoxy-phenyl)-imidazo[1,2-b][1,2,4] triazol-6-yl]-amine,
tert-butyl-[6-(2-methoxy-phenyl)-imidazo[2,1-b]thiazol-5-yl]-amine,
[5-tert-butylamino-6-(2-methoxy-phenyl)-imidazo[2,1-b] thiazol-3-yl]-acetic acid,
tert-butyl-(5-o-tolyl-imidazo[1,2-b][1,2,4]triazol-6-yl)-amine,
tert-butyl-(6-o-tolyl-imidazo[2,1-b]thiazol-5-yl)-amine,
tert-butyl-[5-(2,3-dimethoxy-phenyl)-imidazo[1,2-b][1,2,4] triazol-6-yl]-amine, tert-butyl-[6-(2,3-dimethoxy-phenyl)-imidazo[2,1-b]thiazol-5-yl]-amine,
tert-butyl-(6-p-tolyl-imidazo[2,1-b]thiazol-5-yl)-amine,
(5-tert-butylamino-6-methyl-imidazo[2,1-b]thiazol-3-yl)-acetic acid,
N-tert-butyl-N-(6-phenyl-imidazo[2,1-b]thiazol-5-yl)-acetamide,
N-tert-butyl-N-(6-o-tolyl-imidazo[2,1-b]thiazol-5-yl)-acetamide,
butyl-[6-(4-tert-butyl-phenyl)-2-methyl-imidazo[2,1-b]thiazol-5-yl]amine,
tert-butyl-[5-(2-fluorophenyl)-imidazo[1,2-b][1,2,4]triazol-6-yl]-amine,
tert-butyl-[6-(2-fluorophenyl)-imidazo[2,1-b]thiazol-5-yl]-amine,
tert-butyl-(5-naphthalen-1-yl-imidazo[1,2-b][1,2,4]triazol-6-yl)-amine,
cyclohexyl-(5-naphthalen-1-yl-imidazo[1,2-b][1,2,4]triazol-6-yl)-amine,
[5-(2-bromophenyl)-imidazo[1,2-b][1,2,4]triazol-6-yl]-(1,1,3,3-tetramethyl-butyl)-amine,
N-[4-(6-cyclohexylamino-imidazo[1,2-b][1,2,4]triazol-5-yl)-phenyl]-acetamide,
tert-butyl-[5-(2,5-dimethyl-phenyl)-imidazo[1,2-b][1,2,4]triazol-6-yl]-amine,
cyclohexyl-[6-(2,4-dimethyl-phenyl)-imidazo[2,1-b]thiazol-5-yl]-amine,
cyclohexyl-[6-(2,5-dimethylphenyl)-imidazo[2,1-b]thiazol-5-yl]-amine,
N-tert-butyl-N-(6-p-tolyl-imidazo[2,1-b]thiazol-5-yl)-acetamide,
[5-(2,4-dimethyl-phenyl)-imidazo[1,2-b][1,2,4]triazol-6-yl]-(1,1,3,3-tetramethyl-butyl)-amine,
[5-(2,5-dimethyl-phenyl)-imidazo[1,2-b][1,2,4]triazol-6-yl]-(1,1,3,3-tetramethyl-butyl)-amine,
N-butyl-N-[5-(2-chloro-6-fluorophenyl)-imidazo[1,2-b][1,2,4]triazol-6-yl]-acetamide and
N-butyl-N-[6-(4-tert-butyl-phenyl)-2-methyl-imidazo[2,1-b]thiazol-5-yl]-acetamide, in the form of the base or of pharmaceutically acceptable salts.

The compounds according to the invention are ligands of the pain-relevant α2-subtype of the human α-adrenergic receptor. The use of the bicyclic imidazo-5-yl-amines according to the invention together with one or more auxiliary substances for the preparation of a medicament for combating pain, or method for treating pain comprising administering a pharmaceutically acceptable effective amount of the bicyclic imidazo-5-yl-amines to a patient in need thereof, is therefore particularly preferred.

For the preparation of appropriate medicaments, in addition to at least one active compound according to the invention, carrier materials, fillers, solvents, diluents, dyestuffs, binders and/or other pharmaceutically acceptable excipients are employed. The choice of auxiliary substances and the amounts thereof to be employed depend on whether the medicament is to be administered orally, intravenously, intraperitoneally, intradermally, intramuscularly, intranasally, buccally or locally. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Active compounds according to the invention in a depot, in dissolved form or in a patch, optionally with the addition of agents which promote penetration through the skin, are suitable formulations for percutaneous administration. Formulation forms which can be used orally or percutaneously can release the active compounds according to the invention in a retarded manner.

The amount of active compound to be administered to the patient varies according to the body weight of the patient, and to the mode of administration, the indication and the severity of the disease.

The compounds according to the invention are synthesized by a procedure in which an amidine with the general formula II, in particular 3-aminopyrazole, 3-amino-1,2,4-triazole, 2-amino, 1,3,4-thiadiazole or a 2-aminothiazole derivative, which are commercially available from companies such as Acros, Avocado, Aldrich, Fluka, Lancaster, Maybridge, Merck, Sigma or TCI-Jp, are reacted with the most diverse aldehydes III and isonitriles IV in the presence of 20% perchloric acid in accordance with a three-component reaction to form a compound of the formula Ia (see below). R1 to R3, X and Y here have the meaning given above for compounds of the formula I.

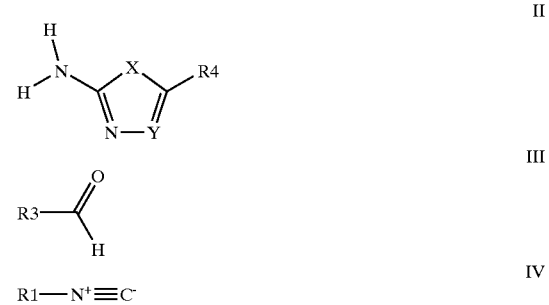

The reactions are preferably carried out in methylene chloride (MC) at a temperature of 0° C. to 40° C., in particular at 10° C. to 20° C.

To prepare the compounds according to the invention in which $R^2$ does not denote hydrogen, the compounds Ia formed in the reaction described above, which have preferably first been dissolved in methylene chloride or THF (5-hydroxymethylene tetrahydrofolate, or tetrahydrofuran), are reacted, depending on the desired end product, with a compound $R^2$Hal, wherein Hal represents bromine, iodine or, in particular, chlorine, for example an optionally substituted alkyl, aryl or acid chloride, or an optionally substituted isocyanate $R^e$NCO in the presence of a morpholine resin (e.g. polystyrene-morpholine from Argonaut) in methylene chloride in the course of 2 to 24 hours at temperatures between 10° C. and 40° C. in accordance with the following equation:

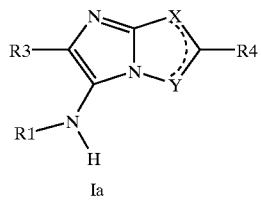

1.) $R^2$Hal or $R^e$NCO polymer-bonded morpholine; MC, T = 10–40° C., 2–24 h
2.) polymer-bonded tris (2-aminoethyl)amine

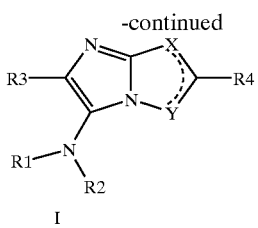

I

The excess reagents are then removed from the reaction mixture by filtration over a layer with polymer-bonded tris(2-aminoethyl)amine (manufacturer: Novabiochem) or 3-(3-mercaptophenyl)propanamidomethylpolystyrene and the filtrate is preferably concentrated in a vacuum centrifuge. The entire process can also easily be carried out in an automated synthesis unit.

The compounds of the formula I can be converted into their pharmaceutically acceptable salts in a manner well-known to those ordinarily skilled in the art with physiologically tolerated acids, preferably hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid, and in particular hydrochloric acid. The salt formation is preferably carried out in a solvent, in particular diethyl ether, diisopropyl ether, acetic acid alkyl esters, acetone or 2-butanone, or a mixture of these solvents. Alternatively, trimethylsilane in aqueous solution is also suitable for preparation of the hydrochlorides.

EXAMPLES

The following examples are intended to illustrate the invention without limiting it thereto.

The synthesis of the compounds was carried out in an automatic unit from Zymark in accordance with the following general synthesis instructions:

A round-bottomed tube of glass (diameter 16 mm, length 125 mm) with a thread was provided manually with a stirrer and closed with a screw-cap with a septum on the capper station. The tube was placed by robot 1 in the reactor block temperature-controlled at 15° C. Robot 2 pipetted in the following reagents in succession:

1.) 1 ml of a 0.1 M amidine solution+20% $HClO_4$ in methylene chloride
2.) 0.5 ml of a 0.3 M aldehyde solution in methylene chloride
3.) 0.575 ml of a 0.2 M isonitrile solution in methylene chloride The reaction mixture was stirred at 15° C. in one of the stirring blocks for 660 min. Thereafter, the reaction solution was filtered at the filtration station. The tube was rinsed here twice with in each case 1 ml methylene chloride and 200 µl water.

The rack with the tubes was then placed manually on the working-up unit. On this, 3 ml of a 10% NaCl solution and 1.5 ml methylene chloride were added to the reaction mixture on a vortexer. The components were mixed thoroughly in the spin reactor for ten minutes and a clear phase boundary was formed by slowly decreasing the rotational movement. This phase boundary was detected optically and the organic phase was pipetted off. In the next step, 1.5 ml methylene chloride were again added to the reaction mixture. The solution was shaken and centrifuged and the organic phase was pipetted off. The combined organic phases were dried over 2.4 g $MgSO_4$ (granulated). The solvent was removed in a vacuum centrifuge.

For the examples in which the compound formed in this way was reacted further with acetyl chloride, this was effected in accordance with the following general instructions:

The product obtained in accordance with the above general synthesis instructions was dissolved in methylene chloride, 4 molar equivalents of acetyl chloride were added and the mixture was stirred at 18° C. for four hours. The excess acetyl chloride and the solvent were removed at 40–60° C. in vacuo.

The chemicals and solvents employed were obtained commercially. Each substance was analysed by ESI-MS and/or NMR.

Example 1 tert-Butyl-(5-furan-2-yl-imidazo[1,2-b][1,2,4]triazol-6-yl)-amine (1)

Compound 1 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) furfural solution (0.3 M, MC) and 10 µl perchloric acid (w=20%) in a substance library.

An ESI-MS was recorded for characterization.

Mass found: 262

Example 2 tert-Butyl-(6-furan-2-yl-imidazo[2,1-b]thiazol-5-yl)-amine (2)

Compound 2 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) furfural solution (0.3 M, MC) and 10 µl perchloric acid (w=20%) in a substance library.

An ESI-MS was recorded for characterization.

Mass found: 262

Example 3

(5 -tert-Butylamino-6-furan-2-yl-imidazo[2,1-b] thiazol-3 -yl)-acetic acid (3)

Compound 3 was prepared in accordance with the general synthesis instructions from 1.0 ml (0.1 mmol) (2-aminothiazol-4-yl)acetic acid solution (0.1 M, MC), 0.575 ml (0.115 mmol) tert-butylisonitrile solution (0.2 M, MC), 0.500 ml (0.15 mmol) furfural solution (0.3 M, MC) and 10 µl perchloric acid (w=20%) in a substance library.

An ESI-MS was recorded for characterization.

Mass found: 320

Example 4 tert-Butyl-(5-pyridin-2-yl-imidazo[1,2-b][1,2,4]triazol-6-yl)-amine (4)

Compound 4 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2-pyridinecarbaldehyde solution (0.3 M, MC) and 10 µl perchloric acid (w=20%) in a substance library.

An ESI-MS was recorded for characterization.

Mass found: 257

Example 5 tert-Butyl-(6-pyridin-2-yl-imidazo[2,1-b]thiazol-5-yl)-amine (5)

Compound 5 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2-pyridinecarbaldehyde solution (0.3 M, MC) and 10 µl perchloric acid (w=20%) in a substance library.

An ESI-MS was recorded for characterization.
Mass found: 273

Example 6 tert-Butyl-(5-pyridin-3-yl-imidazo[1,2-b][1,2,4]triazol-6-yl)-amine (6)

Compound 6 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 3-pyridinecarbaldehyde solution (0.3 M, MC) and 10 µl perchloric acid (w=20%) in a substance library.

An ESI-MS was recorded for characterization.
Mass found: 257

Example 7 tert-Butyl-(5-pyridin-4-yl-imidazo[1,2-b][1,2,4]triazol-6-yl)amine (7)

Compound 7 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 4-pyridinecarbaldehyde solution (0.3 M, MC) and 10 µl perchloric acid (w=20%) in a substance library.

An ESI-MS was recorded for characterization.
Mass found: 257

Example 8 tert-Butyl-(6-cyclohexyl-imidazo[2,1-b]thiazol-5-yl)-amine (8)

Compound 8 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) cyclohexylcarbaldehyde solution (0.3 M, MC) and 10 µl perchloric acid (w=20%) in a substance library.

An ESI-MS was recorded for characterization.
Mass found: 278

Example 9 tert-Butyl-(5-methyl-imidazo[1,2-b][1,2,4]triazol-6-yl)-amine (9)

Compound 9 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) acetaldehyde solution (0.3 M, MC) and 10 µl perchloric acid (w=20%) in a substance library.

An ESI-MS was recorded for characterization.
Mass found: 194

Example 10 tert-Butyl-(6-methyl-imidazo[2,1-b]thiazol-5-yl)-amine (10)

Compound 10 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) aldehyde solution (0.3 M, MC) and 10 µl perchloric acid (w=20%) in a substance library.

An ESI-MS was recorded for characterization.
Mass found: 210

Example 11

Cyclohexyl-(5-pyridin-2-yl-imidazo[1,2-b][1,2,4]triazol-6-yl)-amine (11)

Compound 11 was prepared in accordance with the general synthesis instructions from 1.0 ml (0.1 mmol) 3-amino-1,2,4-triazole solution (0.1 M, MC), 0.575 ml (0.115 mmol) cyclohexylisonitrile solution (0.2 M, MC), 0.500 ml (0.15 mmol) 2-pyridinecarbaldehyde solution (0.3 M, MC) and 10 µl perchloric acid (w=20%) in a substance library.

An ESI-MS was recorded for characterization.
Mass found: 283

Example 12

Cyclohexyl-(6-pyridin-2-yl-imidazo[2,1-b]thiazol-5-yl)-amine (12)

Compound 12 was prepared in accordance with the general synthesis instructions from 1.0 ml (0.1 mmol) 2-aminothiazole solution (0.1 M, MC), 0.575 ml (0.115 mmol) cyclohexylisonitrile solution (0.2 M, MC), 0.500 ml (0.15 mmol) 2-pyridinecarbaldehyde solution (0.3 M, MC) and 10 µl perchloric acid (w=20%) in a substance library.

An ESI-MS was recorded for characterization.
Mass found: 299

Example 13

(5-Cyclohexylamino-6-pyridin-2-yl-imidazo[2,1-b]thiazol-3-yl)-acetic acid (13)

Compound 13 was prepared in accordance with the general synthesis instructions from 1.0 ml (0.1 mmol) (2-aminothiazol-4-yl)acetic acid solution (0.1 M, MC), 0.575 ml (0.115 mmol) cyclohexylisonitrile solution (0.2 M, MC), 0.500 ml (0.15 mmol) 3-pyridinecarbaldehyde solution (0.3 M, MC) and 10 µl perchloric acid (w=20%) in a substance library.

An ESI-MS was recorded for characterization.
Mass found: 357

Example 14

Cyclohexyl-(6-pyridin-4-yl-imidazo[2,1-b]thiazol-5-yl)-amine (14)

Compound 14 was prepared in accordance with the general synthesis instructions from 1.0 ml (0.1 mmol) 2-aminothiazole solution (0.1 M, MC), 0.575 ml (0.115 mmol) cyclohexylisonitrile solution (0.2 M, MC), 0.500 ml (0.15 mmol) 3-pyridinecarbaldehyde solution (0.3 M, MC) and 10 µl perchloric acid (w=20%) in a substance library.

An ESI-MS was recorded for characterization.

Mass found: 299

Example 15

Cyclohexyl-(6-cyclohexyl-imidazo[2,1-b]thiazol-5-yl)-amine (15)

Compound 15 was prepared in accordance with the general synthesis instructions from 1.0 ml (0.1 mmol) 2-aminothiazole solution (0.1 M, MC), 0.575 ml (0.115 mmol) cyclohexylisonitrile solution (0.2 M, MC), 0.500 ml (0.15 mmol) cyclohexylcarbaldehyde solution (0.3 M, MC) and 10 µl perchloric acid (w=20%) in a substance library.
An ESI-MS was recorded for characterization.
Mass found: 304

Example 16

(6-Cyclohexyl-5-cyclohexylamino-imidazo[2,1-b]thiazol-3-yl)-acetic acid (16)

Compound 16 was prepared in accordance with the general synthesis instructions from 1.0 ml (0.1 mmol) (2-aminothiazol-4-yl)acetic acid solution (0.1 M, MC), 0.575 ml (0.115 mmol) cyclohexylisonitrile solution (0.2 M, MC), 0.500 ml (0.15 mmol) cyclohexylcarbaldehyde solution (0.3 M, MC) and 10 µl perchloric acid (w=20%) in a substance library.
An ESI-MS was recorded for characterization.
Mass found: 318

Example 17

(5-Cyclohexylamino-6-methyl-imidazo[2,1-b]thiazol-3-yl)-acetic acid (17)

Compound 17 was prepared in accordance with the general synthesis instructions from 1.0 ml (0.1 mmol) (2-aminothiazol-4-yl)acetic acid solution (0.1 M, MC), 0.575 ml (0.115 mmol) cyclohexylisonitrile solution (0.2 M, MC), 0.500 ml (0.15 mmol) acetaldehyde solution (0.3 M, MC) and 10 µl perchloric acid (w=20%) in a substance library.
An ESI-MS was recorded for characterization.
Mass found: 250

Example 18

(2,6-Dimethyl-phenyl)-(5-furan-2-yl-imidazo[1,2-b][1,2,4]triazol-6-yl)-amine (18)

Compound 18 was prepared in accordance with the general synthesis instructions from 1.0 ml (0.1 mmol) 3-amino-1,2,4-triazole solution (0.1 M, MC), 0.575 ml (0.115 mmol) 2,6-dimethylphenylisonitrile solution (0.2 M, MC), 0.500 ml (0.15 mmol) furfural solution (0.3 M, MC) and 10 µl perchloric acid (w=20%) in a substance library.
An ESI-MS was recorded for characterization.
Mass found: 292

Example 19

(2,6-Dimethyl-phenyl)-(6-pyridin-2-yl-imidazo[2,1-b]thiazol-5-yl)-amine (19)

Compound 19 was prepared in accordance with the general synthesis instructions from 1.0 ml (0.1 mmol) 2-aminothiazole solution (0.1 M, MC), 0.575 ml (0.115 mmol) 2,6-dimethylphenylisonitrile solution (0.2 M, MC), 0.500 ml (0.15 mmol) 2-pyridinecarbaldehyde solution (0.3 M, MC) and 10 µl perchloric acid (w=20%) in a substance library.
An ESI-MS was recorded for characterization.
Mass found: 321

Example 20

(2,6-dimethyl-phenyl)-(6-pyridin-3-yl-imidazo[2,1-b]thiazol-5-yl)-amine (20)

Compound 20 was prepared in accordance with the general synthesis instructions from 1.0 ml (0.1 mmol) 2-aminothiazole solution (0.1 M, MC), 0.575 ml (0.115 mmol) 2,6-dimethylphenylisonitrile solution (0.2 M, MC), 0.500 ml (0.15 mmol) 3-pyridinecarbaldehyde solution (0.3 M, MC) and 10 µl perchloric acid (w=20%) in a substance library.
An ESI-MS was recorded for characterization.
Mass found: 321

Example 21

(2,6-Dimethyl-phenyl)-(6-pyridin-4-yl-imidazo[2,1-b]thiazol-5-yl)-amine (21)

Compound 21 was prepared in accordance with the general synthesis instructions from 1.0 ml (0.1 mmol) 2-aminothiazole solution (0.1 M, MC), 0.575 ml (0.115 mmol) 2,6-dimethylphenylisonitrile solution (0.2 M, MC), 0.500 ml (0.15 mmol) 4-pyridinecarbaldehyde solution (0.3 M, MC) and 10 µl perchloric acid (w=20%) in a substance library.
An ESI-MS was recorded for characterization.
Mass found: 321

Example 22

Methyl (6-cyclohexyl-imidazo[2,1-b]thiazol-5-ylamino)-acetate (22)

Compound 22 was prepared in accordance with the general synthesis instructions from 1.0 ml (0.1 mmol) 2-aminothiazole solution (0.1 M, MC), 0.575 ml (0.115 mmol) methyl isocyanoacetate solution (0.2 M, MC), 0.500 ml (0.15 mmol) cyclohexylcarbaldehyde solution (0.3 M, MC) and 10 µl perchloric acid (w=20%) in a substance library.
An ESI-MS was recorded for characterization.
Mass found: 294

Example 23

Methyl (6-methyl-imidazo[2,1-b]thiazol-5-ylamino)-acetate (23)

Compound 23 was prepared in accordance with the general synthesis instructions from 1.0 ml (0.1 mmol) 2-aminothiazole solution (0.1 M, MC), 0.575 ml (0.115 mmol) methyl isocyanoacetate solution (0.2 M, MC), 0.500 ml (0.15 mmol) acetaldehyde solution (0.3 M, MC) and 10 µl perchloric acid (w=20%) in a substance library.
An ESI-MS was recorded for characterization.
Mass found: 226

Example 24 tert-Butyl-(2-phenyl-5H-imidazo[1,2-b]pyrazol-3-yl)-amine (24)

Compound 24 was prepared in accordance with the general synthesis instructions from 1.0 ml (0.1 mmol) 3-aminopyrazole solution (0.1 M, MC), 0.575 ml (0.115 mmol) tert-butylisonitrile solution (0.2 M, MC), 0.500 ml (0.15 mmol) benzaldehyde solution (0.3 M, MC) and 10 µl perchloric acid (w=20%) in a substance library.

An ESI-MS was recorded for characterization.
Mass found: 255

Example 25

3-(5-tert-Butylamino-imidazo[2,1-b]thiazol-6-yl)-phenol (25)

Compound 25 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 3-hydroxybenzaldehyde solution (0.3 M, MC) and 10 µl perchloric acid (w=20%) in a substance library.

An ESI-MS was recorded for characterization.
Mass found: 288

Example 26 tert-Butyl-[6-(3,4-dimethoxy-phenyl)-imidazo[2,1-b]thiazol-5-yl]-amine (26)

Compound 26 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 3,4-dimethoxybenzaldehyde solution (0.3 M, MC) and 10 µl perchloric acid (w=20%) in a substance library.

An ESI-MS was recorded for characterization.
Mass found: 332

Example 27 tert-Butyl-[5-(2,3-dichloro-phenyl)-imidazo[1,2-b][1,2,4]triazol-6-yl]-amine (27)

Compound 27 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2,3-dichlorobenzaldehyde solution (0.3 M, MC) and 10 µl perchloric acid (w=20%) in a substance library.

An ESI-MS was recorded for characterization.
Mass found: 324

Example 28 tert-Butyl-[6-(2,3-dichloro-phenyl)-imidazo[2,1-b]thiazol-5-yl]-amine (28)

Compound 28 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2,3-dichlorobenzaldehyde solution (0.3 M, MC) and 10 µl perchloric acid (w=20%) in a substance library.

An ESI-MS was recorded for characterization.
Mass found: 340

Example 29 tert-Butyl-[5-(2,4-dichloro-phenyl)-imidazo[1,2-b](1,2,4]triazol-6-yl]-amine (29)

Compound 29 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2,4-dichlorobenzaldehyde solution (0.3 M, MC) and 10 µl perchloric acid (w=20%) in a substance library.

An ESI-MS was recorded for characterization.
Mass found: 324

Example 30 tert-Butyl-[6-(2,4-dichloro-phenyl)-imidazo[2,1-b]thiazol-5-yl]-amine (30)

Compound 30 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2,4-dichlorobenzaldehyde solution (0.3 M, MC) and 10 µl perchloric acid (w=20%) in a substance library.

An ESI-MS was recorded for characterization.
Mass found: 340

Example 31 tert-Butyl-[5-(2-methoxy-phenyl)-imidazo[1,2-b][1,2,4]triazol-6-yl]-amine (31)

Compound 31 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2-methoxybenzaldehyde solution (0.3 M, MC) and 10 µl perchloric acid (w=20%) in a substance library.

An ESI-MS was recorded for characterization.
Mass found: 286

Example 32 tert-Butyl-[6-(2-methoxy-phenyl)-imidazo[2,1-b]thiazol-5-yl]-amine (32)

Compound 32 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2-methoxybenzaldehyde solution (0.3 M, MC) and 10 µl perchloric acid (w=20%) in a substance library.

An ESI-MS was recorded for characterization.
Mass found: 302

Example 33

[5-tert-Butylamino-6-(2-methoxy-phenyl)-imidazo[2,1-b]thiazol-3-yl]-acetic acid (33)

Compound 33 was prepared in accordance with the general synthesis instructions from 1.0 ml (0.1 mmol) (2-aminothiazol-4-yl)acetic acid solution (0.1 M, MC), 0.575 ml (0.115 mmol) tert-butylisonitrile solution (0.2 M, MC), 0.500 ml (0.15 mmol) 2-methoxybenzaldehyde solution (0.3 M, MC) and 10 µl perchloric acid (w=20%) in a substance library.

An ESI-MS was recorded for characterization.
Mass found: 321

Example 34 tert-Butyl-(5-o-tolyl-imidazo[1,2-b][1,2,4]triazol-6-yl)-amine (34)

Compound 34 was prepared in accordance with the general synthesis instructions from 1.0 ml (0.1 mmol) 3-amino- 1,2,4-triazole solution (0.1 M, MC), 0.575 ml (0.115 mmol) tert-butylisonitrile solution (0.2 M, MC), 0.500 ml (0.15 mmol) 2-methylbenzaldehyde solution (0.3 M, MC) and 10 µl perchloric acid (w=20%) in a substance library.

An ESI-MS was recorded for characterization.

Mass found: 270

Example 35 tert-Butyl-(6-o-tolyl-imidazo[2,1-b]thiazol-5-yl)-amine (35)

Compound 35 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2-methylbenzaldehyde solution (0.3 M, MC) and 10 µl perchloric acid (w=20%) in a substance library.

An ESI-MS was recorded for characterization.

Mass found: 321

Example 36 tert-Butyl- [5-(2,3-dimethoxy-phenyl)-imidazo[1,2-b][1,2,4]triazol-6-yl]-amine (36)

Compound 36 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2,3-dimethoxybenzaldehyde solution (0.3 M, MC) and 10 µl perchloric acid (w=20%) in a substance library.

An ESI-MS was recorded for characterization.

Mass found: 316

Example 37 tert-Butyl-[6-(2,3-dimethoxy-phenyl)-imidazo[2,1-b]thiazol-5-yl]-amine (37)

Compound 37 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2,3-dimethoxybenzaldehyde solution (0.3 M, MC) and 10 µl perchloric acid (w=20%) in a substance library.

An ESI-MS was recorded for characterization.

Mass found: 332

Example 38 tert-Butyl-(6-p-tolyl-imidazo[2,1-b]thiazol-5-yl)-amine (38)

Compound 38 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 4-methylbenzaldehyde solution (0.3 M, MC) and 10 µl perchloric acid (w=20%) in a substance library.

An ESI-MS was recorded for characterization.

Mass found: 286

Example 39

(5-tert-Butylamino-6-methyl-imidazo[2,1-b]thiazol-3-yl)-acetic acid (39)

Compound 39 was prepared in accordance with the general synthesis instructions from 1.0 ml (0.1 mmol) (2-amino-thiazol-4-yl)-acetic acid solution (0.1 M, MC), 0.575 ml (0.115 mmol) tert-butylisonitrile solution (0.2 M, MC), 0.500 ml (0.15 mmol) acetaldehyde solution (0.3 M, MC) and 10 µl perchloric acid (w=20%) in a substance library.

An ESI-MS was recorded for characterization.

Mass found: M-$CO_2$ 224.3

Example 40

N-tert-Butyl-N-(6-phenyl-imidazo[2,1-b]thiazol-5-yl)-acetamide (40)

Compound 40 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) benzaldehyde solution (0.3 M, MC) and 10 µl perchloric acid (w=20%) and by reaction with acetyl chloride, the excess acetyl chloride being removed in vacuo.

An ESI-MS was recorded for characterization.

Mass found: 315.3, M-acetyl 272.1

Example 41

N-tert-Butyl-N-(6-o-tolyl-imidazo[2,1-b]thiazol-5-yl)-acetamide (41)

Compound 41 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 2-methylbenzaldehyde solution (0.3 M, MC) and 10 µl perchloric acid (w=20%) and by reaction with acetyl chloride, the excess acetyl chloride being removed in vacuo An ESI-MS was recorded for characterization.

Mass found: M-acetyl 286.3

Example 42

Butyl-[6-(4-tert-butyl-phenyl)-2-methyl-imidazo[2,1-b]thiazol-5-yl]-amine (42)

Compound 42 was prepared in accordance with the general synthesis instructions from 1.0 ml (0.1 mmol) 5-methyl-thiazol-2-yl-amine solution (0.1 M, MC), 0.575 ml (0.115 mmol) n-butylisonitrile solution (0.2 M, MC), 0.500 ml (0.15 mmol) 4-tert-butylbenzaldehyde solution (0.3 M, MC) and 10 µl perchloric acid (w 20%) in a substance library.

An ESI-MS was recorded for characterization.

Mass found: 342.3

Example 43 tert-Butyl-[5-(2-fluorophenyl)-imidazo[1,2-b][1,2,4]triazol-6-yl]-amine (43)

Compound 43 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2-fluorobenzaldehyde solution (0.3 M, MC) and 10 µl perchloric acid (w=20%) in a substance library.

An ESI-MS was recorded for characterization.

Mass found: 274.1

Example 44 tert-Butyl-[6-(2-fluorophenyl)-imidazo[2,1-b]thiazol-5-yl]-amine (44)

Compound 44 was prepared in accordance with the general synthesis instructions from 1.0 ml (0.1 mmol)

2-aminothiazole solution (0.1 M, MC), 0.575 ml (0.115 mmol) tert-butylisonitrile solution (0.2 M, MC), 0.500 ml (0.15 mmol) 2-fluorobenzaldehyde solution (0.3 M, MC) and 10 µl perchloric acid (w=20%) in a substance library.

An ESI-MS was recorded for characterization.
Mass found: 290.2

Example 45 tert-Butyl-(5-naphthalen-1-yl-imidazo[1,2-b][1,2,4] triazol-6-yl)-amine (45)

Compound 45 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 1-naphthylcarbaldehyde solution (0.3 M, MC) and 10 µl perchloric acid (w=20%) in a substance library.

An ESI-MS was recorded for characterization.
Mass found: 306.2

Example 46

Cyclohexyl-(5-naphthalen-1-yl-imidazo[1,2-b][1,2,4]triazol-6-yl)-amine (46)

Compound 46 was prepared in accordance with the general synthesis instructions from 1.0 ml (0.1 mmol) 3-amino-1,2,4-triazole solution (0.1 M, MC), 0.575 ml (0.115 mmol) cyclohexylisonitrile solution (0.2 M, MC), 0.500 ml (0.15 mmol) 1-naphthylcarbaldehyde solution (0.3 M, MC) and 10 µl perchloric acid (w=20%) in a substance library.

An ESI-MS was recorded for characterization.
Mass found: 332.3

Example 47

[5-(2-Bromophenyl)-imidazo[1,2-b][1,2,4]triazol-6-yl]-(1,1,3,3-tetramethyl-butyl)-amine (47)

Compound 47 was prepared in accordance with the general synthesis instructions from 1.0 ml (0.1 mmol) 3-amino-1,2,4-triazole solution (0.1 M, MC), 0.575 ml (0.115 mmol) 1,1,3,3-tetramethylbutylisonitrile solution (0.2 M, MC), 0.500 ml (0.15 mmol) 2-bromobenzaldehyde solution (0.3 M, MC) and 10 µl perchloric acid (w=20%) in a substance library.

An ESI-MS was recorded for characterization.
Mass found: 390.3/392.2

Example 48

N-[4-(6-Cyclohexylamino-imidazo[1,2-b][1,2,4] triazol-5-yl)-phenyl]-acetamide (48)

Compound 48 was prepared in accordance with the general synthesis instructions from 1.0 ml (0.1 mmol) 3-amino-1,2,4-triazole solution (0.1 M, MC), 0.575 ml (0.115 mmol) cyclohexylisonitrile solution (0.2 M, MC), 0.500 ml (0.15 mmol) N-(4-formyl-phenyl)-acetamide solution (0.3 M, MC) and 10 µl perchloric acid (w=20%) in a substance library.

An ESI-MS was recorded for characterization.
Mass found: 337.1

Example 49 tert-Butyl-[5-(2,5-dimethyl-phenyl)-imidazo[1,2-b][1,2,4]triazol-6-yl]-amine (49)

Compound 49 was prepared in accordance with the general synthesis instructions from 1.0 ml (0.1 mmol) 3-amino-1,2,4-triazole solution (0.1 M, MC), 0.575 ml (0.115 mmol) tert-butylisonitrile solution (0.2 M, MC), 0.500 ml (0.15 mmol) 2,5-dimethylbenzaldehyde solution (0.3 M, MC) and 10 µl perchloric acid (w=20%) in a substance library.

An ESI-MS was recorded for characterization.
Mass found: 284.2

Example 50

Cyclohexyl-[6-(2,4-dimethyl-phenyl)-imidazo[2,1-b] thiazol-5-yl]-amine (50)

Compound 50 was prepared in accordance with the general synthesis instructions from 1.0 ml (0.1 mmol) 2-aminothiazole solution (0.1 M, MC), 0.575 ml (0.115 mmol) cyclohexylisonitrile solution (0.2 M, MC), 0.500 ml (0.15 mmol) 2,4-dimethylbenzaldehyde solution (0.3 M, MC) and 10 µl perchloric acid (w=20%) in a substance library.

An ESI-MS was recorded for characterization.
Mass found: 326.3

Example 51

Cyclohexyl-[6-(2,5-dimethylphenyl)-imidazo[2,1-b] thiazol-5-yl]-amine (51)

Compound 51 was prepared in accordance with the general synthesis instructions from 1.0 ml (0.1 mmol) 2-aminothiazole solution (0.1 M, MC), 0.575 ml (0.115 mmol) cyclohexylisonitrile solution (0.2 M, MC), 0.500 ml (0.15 mmol) 2,5-dimethylbenzaldehyde solution (0.3 M, MC) and 10 µl perchloric acid (w=20%) in a substance library.

An ESI-MS was recorded for characterization.
Mass found: 326.3

Example 52

N-tert-Butyl-N-(6-p-tolyl-imidazo[2,1-b]thiazol-5-yl)-acetamide (52)

Compound 52 was prepared in accordance with the general synthesis instructions from 1.0 ml (0.1 mmol) 2-aminothiazole solution (0.1 M, MC), 0.575 ml (0.115 mmol) tert-butylisonitrile solution (0.2 M, MC), 0.500 ml (0.15 mmol) 4-methylbenzaldehyde solution (0.3 M, MC) and 10 µl perchloric acid (w=20%) and by reaction with acetyl chloride, the excess acetyl chloride being removed in vacuo.

An ESI-MS was recorded for characterization.
Mass found: 327.4, M-acetyl 286.3

Example 53

[5-(2,4-dimethyl-phenyl)-imidazo[1,2-b][1,2,4] triazol-6-yl]-(1,1,3,3-tetramethyl-butyl)-amine (53)

Compound 53 was prepared in accordance with the general synthesis instructions from 1.0 ml (0.1 mmol) 3-amino-1,2,4-triazole solution (0.1 M, MC), 0.575 ml (0.115 mmol) 1,1,3,3-tetramethylbutylisonitrile solution (0.2 M, MC), 0.500 ml (0.15 mmol) 2,4-dimethylbenzaldehyde solution (0.3 M, MC) and 10 µl perchloric acid (w=20%).

An ESI-MS was recorded for characterization.
Mass found: 340.2

Example 54

[5-(2,5-Dimethyl-phenyl)-imidazo[1,2-b][1,2,4] triazol-6-yl]-(1,1,3,3-tetramethyl-butyl)-amine (54)

Compound 54 was prepared in accordance with the general synthesis instructions from 1.0 ml (0.1 mmol) 3-amino- 1,2,4-triazole solution (0.1 M, MC), 0.575 ml (0.115 mmol) 1,1,3,3-tetramethylbutylisonitrile solution (0.2 M, MC), 0.500 ml (0.15 mmol) 2,5-dimethylbenzaldehyde solution (0.3 M, MC) and 10 μl perchloric acid (w=20%).

An ESI-MS was recorded for characterization.

Mass found: 340.2

Example 55

N-Butyl-N-[5-(2-chloro-6-fluorophenyl)-imidazo[1,2-b][1,2,4]triazol-6-yl]-acetamide (55)

Compound 55 was prepared in accordance with the general synthesis instructions from 1.0 ml (0.1 mmol) 3-amino-1,2,4-triazole solution (0.1 M, MC), 0.575 ml (0.115 mmol) n-butylisonitrile solution (0.2 M, MC), 0.500 ml (0.15 mmol) 2-chloro-6-fluorobenzaldehyde solution (0.3 M, MC) and 10 μl perchloric acid (w=20%) and by reaction with acetyl chloride, the excess acetyl chloride being removed in vacuo.

An ESI-MS was recorded for characterization.

Mass found: 350.4

Example 56

N-Butyl-N-[6-(4-tert-butyl-phenyl)-2-methyl-imidazo[2,1-b]thiazol-5-yl]-acetamide (56)

Compound 56 was prepared in accordance with the general synthesis instructions from 1.0 ml (0.1 mmol) 2-amino-5-methylthiazole solution (0.1 M, MC), 0.575 ml (0.115 mmol) n-butylisonitrile solution (0.2 M, MC), 0.500 ml (0.15 mmol) 4-tert-butylbenzaldehyde solution (0.3 M, MC) and 10 μl perchloric acid (w=20%) and by reaction with acetyl chloride, the excess acetyl chloride being removed in vacuo.

An ESI-MS was recorded for characterization.

Mass found: 384.5

The compounds according to the invention are ligands of the pain-relevant α2-subtype of the human α-adrenergic receptor. The affinity for the α2-subtype of the human α-adrenergic receptor was determined by means of a conventional SPA assay for high throughput screening, such as is described in John P. Devlin, High Throughput Screening, Marcel Dekker Inc. 1997, page 307 to 316. This literature is incorporated herein by reference and thus forms part of the disclosure. The following affinities were determined at a concentration of 10 μM:

|  | alpha2 affinity, 10 μM |
|---|---|
| Example 39 | 35% |
| Example 40 | 77% |
| Example 41 | 50% |
| Example 42 | 36% |
| Example 43 | 34% |
| Example 44 | 38% |
| Example 45 | 41% |
| Example 46 | 46% |
| Example 47 | 42% |
| Example 48 | 36% |
| Example 49 | 38% |
| Example 50 | 36% |
| Example 51 | 39% |
| Example 52 | 51% |
| Example 53 | 43% |
| Example 54 | 56% |

-continued

|  | alpha2 affinity, 10 μM |
|---|---|
| Example 55 | 39% |
| Example 56 | 46% |

The foregoing disclosure has been set forth merely to illustrate the invention and is not intended to be limiting. Since modifications of the disclosed embodiments incorporating the spirit and substance of the invention may occur to persons skilled in the art, the invention should be construed to broadly include everything within the scope of the appended claims and equivalents thereof.

We claim:

1. A bicyclic imidazo-5-yl-amine of formula I

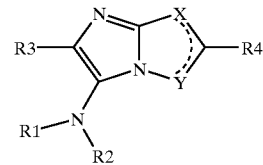

wherein

R$^1$ denotes C(CH$_3$)$_3$; (CE$_2$)$_6$ ON; optionally substituted phenyl; C$_4$–C$_8$-cycloalkyl; CH$_2$OH$_2$R (R=4-morpholino); 1,1,3,8-tetramethylbutyl; or CH$_2$R$^a$, wherein R$^a$ represents hydrogen, branched or unbranched C$_1$–C$_8$-alkyl, optionally substituted phenyl, CO(OR') (where R'=branched or unbranched C$_1$–C-alkyl), PO(OR")$_2$ (where R"=branched or unbranched C$_1$–C$_4$-alkyl) or Si(R$^x$R$^y$R$^z$) (where R$^x$, R$^y$ and R$^z$ in each case independently of one another are branched or unbranched C$_1$–C$_8$-alkyl, C$_4$–C$_8$-cycloalkyl or phenyl), R$^2$ denotes hydrogen; COR$^b$, wherein R$^b$ represents hydrogen, branched or unbranched C–C$_8$-alkyl, C$_3$–C$_8$-cycloalkyl, CH$_2$CH$_2$CO(OR') (where R'=branched or unbranched C$_1$–C$_8$-alkyl), adamantyl, optionally substituted phenyl, optionally substituted 1-naphthyl, 2-naphthyl, 2-pyridyl, 3-pyridyl, 4-pyridyl, thiazolyl or furoyl; CH$_2$R$^c$, wherein R$^c$ represents hydrogen, branched or unbranched C$_1$–C$_8$-alkyl or optionally substituted phenyl; CH$_2$CH$_2$R$^d$, wherein R$^d$ represents optionally substituted phenyl; or CONHR$^e$, wherein R$^e$ represents phenyl, R$^3$ denotes branched or unbranched C$_1$–C$_8$-alkyl, C$_3$–C$_8$-cycloalkyl, optionally substituted phenyl, optionally substituted 1-naphthyl, 2-naphthyl, quinoline, anthracene, phenanthrene, benzothiophene, benzofurfuryl, optionally substituted pyrrole, 2-pyridyl, 3-pyridyl, 4-pyridyl, optionally substituted furfuryl or optionally substituted thiophene, X denotes CR$^5$ or N, and Y is N, R$^4$ and R$^5$ independently of one another denote hydrogen; branched or unbranched C$_1$–C$_8$-alkyl; fluorine; chlorine; bromine; CF$_3$; CN; NO$_2$; NHR$^f$, wherein R$^f$ represents hydrogen, branched or unbranched C$_1$–C$_8$-alkyl or optionally substituted phenyl; SR$^G$, wherein R$^G$ represents hydrogen, branched or unbranched C$_1$–C$_8$-alkyl, phenyl, pyridine, benzyl or fluorenyl; OR$^h$, wherein R$^h$ represents branched or unbranched C$_1$–C$_8$- alkyl, optionally substituted phenyl or CO(OR') (R'= branched or unbranched $C_1$–$C_8$-alkyl); CO(OR') or $CH_2CO(OR')$, wherein R' in each case has the abovementioned meaning or in the case of the group $CH_2CO$ (OR') also denotes hydrogen, or an optionally substitute phenyl group, wherein optionally substituted phenyl, optionally substituted 1-naphthyl, optionally substituted pyrrole, optionally substituted furfuryl, optionally substituted thiophene, and optionally substituted alkyl is optionally substituted by one or more substituents selected from the group consisting of a halogen atom, cyano group, nitro group, carboxyl group, hydroxyl group, $C_1$–$C_4$ alkylamido group, $C_1$–$C_4$ alkylamino group, pyrrolidino group, branched or unbranched $C_1$–$C_6$ alkyl group, $C_1$–$C_4$ alkyl group substituted with one or more halogen atoms, $C_1$–$C_4$alkoxy group, $C_1$–$C_4$ alkoxy group substituted with one or more halogen atoms, and halogen substituted phenoxy group, or a pharmaceutically acceptable salt thereof, excluding compounds in which simultaneously $R^1$ denotes $C(CH_3)_3$, $R^2$ denotes hydrogen, $R^3$ denotes unsubstituted phenyl, and Y denotes N, or simultaneously $R^1$ denotes $C(CH_3)_3$ $R^2$ denotes hydrogen, $R^8$ denotes unsubstituted phenyl, Y denotes NH, and X denotes N or $CR^5$, where $R^5=CO_2$ethyl.

2. A bicyclic imidazo-5-yl-amine according to claim 1, wherein $R^3$ is a substituted phenyl group selected from the group consisting of 4-acetamidophenyl, 2-bromophenyl, 3-bromophenyl, 4-bromophenyl, 4-bromo-2fluorophenyl, 5-bromo-2-fluorophenyl, 3-bromo-4-fluorophenyl, 4 tert-butylphenyl, 2-chloro-4-fluorophenyl, 2-chloro-6-fluorophenyl, 2-chlorophenyl, 3-chlorophenyl, 4-chlorophenyl, 4-cyanophenyl, 2,3-dichlorophenyl, 2,4-dichlorophenyl, 3,4-dichlorophenyl, 2,3-dimethoxyphenyl, 3,4-dimethoxyphenyl, 2,4-dimethylphenyl, 2,5-dimethylphenyl, 2-fluorophenyl, 3-fluorophenyl, 4-fluorophenyl, 4-hexylphenyl, 3-hydroxyphenyl, 2methoxyphenyl, 2-methylphenyl, 3-methylphenyl, 4-methylphenyl, 4-nitrophenyl, 3-phenoxyphenyl, 4-(1-pyrrolidino)phenyl, 2-(trifluoromethyl)phenyl, 3-(trifluoromethyl)phenyl, 4-(trifluoromethyl)phenyl, 3,4,5-trimethoxyphenyl, 3-(4-chlorophenoxy)phenyl and 4-acetoxy-3-methoxyphenyl, or $R^3$ is a substituted 1-naphthyl group selected from the group consisting of 4-dimethylaminonaphthyl, 2-ethoxynaphthyl and 4-methoxynaphthyl, or $R^2$ is a substituted pyrrole group selected from the group consisting of 2-(1-(phenylsulfonyl)pyrrole), 2-(N-methylpyrrole), 2-(N-(3,5-dichlorophenyl) pyrrole and 2-(1-(4-chlorophenyl)pyrrole), or $R^3$ is a substituted furfuryl group selected from the group consisting of 2-(5-acetoxymethylfurfuryl), 2(5-methylfurfuryl), 2-(5-nitrofurfuryl), 2- [5-(3-nitrophenyl)furfuryl], 2-[5-(2-nitrophenyl)furfuryl], 2-(5-bromofurfuryl), 2-[5-(3(4-chlorophenyl)furfuryl], 2-(4,5-dimethylfurfuryl), 2- [5-(2-chlorophenyl) furfuryl], 2-(5-ethylfurfuryl) and 2- [5-(1,3-dioxalane) furfuryl], or $R^3$ is a substituted thiophene group, selected from the group consisting of 2-(5-chlorothiophenyl), 2-(5-methylthiophenyl), 2-(5-ethylthiophenyl), 2-(3-methylthiophenyl), 2-(4-bromothiophenyl), 2-(5-nitrothiophenyl), 5-(2-carboxythiophenyl), 2-[4-(phenylethyl)thiophenyl], 2-[5-(methylthio) thiophenyl], 2-(3-bromothiophenyl), 2-(3-phenoxythiophenyl) and 2-(5-bromothiophenyl).

3. A bicyclic imidazo-5-amine according to claim 1, wherein $R^b$ is a substituted phenyl group selected from the group consisting of 3,5-bis(trifluoromethyl)phenyl, 2-bromophenyl, 2-fluorophenyl, pentafluorophenyl, 2,4-difluorophenyl, 2,6-difluorophenyl, 2-chlorophenyl, 2,4-dichlorophenyl, 2-acetylphenyl, 2-methoxyphenyl, 2,6-dimethoxyphenyl, 2-(trifluoromethyl)phenyl, 2-methylphenyl, 3-bromophenyl, 3-fluorophenyl, 3-chlorophenyl, 3,4-dichlorophenyl, 3-methoxyphenyl, 3,4-dimethoxyphenyl, 3,4,5-trimethoxyphenyl, 3,5-dimethoxyphenyl, 3-(trifluoromethyl)phenyl, 3-methoxyphenyl, 4-bromophenyl, 4-fluorophenyl, 4-chlorophenyl, 4-methoxyphenyl, 4-(trifluoromethyl) phenyl, 4-tert-butylphenyl, 4-methylphenyl, 2-iodophenyl, 4-iodophenyl, 4-cyanophenyl, 2-nitrophenyl, 3-nitrophenyl, 3,5-dinitrophenyl, 4-nitrophenyl, 3,5-dichlorophenyl, 2,5-difluorophenyl, 2,4-dimethoxyphenyl, 3-nitro-4-methylphenyl, 2,5-dichlorophenyl, 2,3-difluorophenyl, 4-(trifluoromethoxy)phenyl, 2-(trifluoromethoxy)phenyl, and 3-(trifluoromethoxy)phenyl.

4. A bicyclic imidazo-5-yl-amine according to claim 1, wherein $R^c$ is a substituted phenyl group selected from the group consisting of 2-fluorophenyl, 2-chlorophenyl, 2-methylphenyl 2-(trifluoromethyl)phenyl, 2-bromophenyl, 3-methoxyphenyl, 3-nitrophenyl, 3-chlorophenyl, 3-fluorophenyl, 3-phenoxyphenyl, 3-(trifluoromethoxy) phenyl, 3-bromophenyl, 3-chlorophenyl, 3-methylphenyl, 4-tart-butylphenyl, 4-fluorophenyl, 4-chlorophenyl, 4-vinylphenyl, 4-(trifluoromethoxy)phenyl, 3,5-dimethoxyphenyl, 3,5-difluorophenyl, 3,5-di (trifluoromethyl)phenyl, 3,5-difluorophenyl, 3,5-dimethylphenyl 2,3-dichlorophenyl, 2,3-dimethylphenyl 2,3-difluorophenyl, 3-chloro-2-fluorophenyl, 2-chloro-4-fluorophenyl, 2,4-di(trifluoromethyl)phenyl, 2,4-dichlorophenyl, 2,4-difluorophenyl, 2,4-dimethylphenyl, 2,5-dichlorophenyl, 2,5-dimethylphenyl, 2,5-difluorophenyl, 3,4-dichlorophenyl, 3,4-difluorophenyl, 3,4-dimethylphenyl, 2,3,4-trifluorophenyl, 2,3,6-trifluorophenyl, 2,4,5-trifluorophenyl, 2,4,6-trimethylphenyl and pentafluorophenyl.

5. A bicyclic imidazo-5-yl-amine according to claim 1, wherein $R^d$ is a substituted phenyl group selected from the group consisting of 3-chlorophenyl, 4-chlorophenyl, 4-carboxyphenyl, 4-acetylphenyl, 4-methoxyphenyl, 4-fluorophenyl, 4-nitrophenyl and 4-hydroxyphenyl.

6. A bicyclic imidazo-5-yl-amine selected from the group consisting of tert-butyl-(5-furan-2-yl-imidazo[1,2-b][1,2,4]triazol-6-yl)-amine, tert-butyl-(5-pyridin-2-yl-imidazo[1,2-b][1,2,4]triazol-6-yl)-amine, tert-butyl-(5-pyridin-3-yl-imidazo[1,2-b][1,2,4]triazol-6-yl)-amine, tert-butyl-(5-pyridin-4-yl-imidazo[1,2-b][1,2,4]triazol-6-yl)-amine, tert-butyl-(5-methyl-imidazo[1,2-b]1,2,4]triazol-6-yl)-amine, cyclohexyl-(5-pyridin-2-yl-imidazo[1,2-b][1,2,4]triazol-6-yl)-amine, (2,6-dimethyl-phenyl)-(5-furan-2-yl-imidazo[1,2-b][1,2,4]triazol-6-yl)-amine, tert-butyl-(2-phenyl-5H-imidazo[1,2-b]pyrazol-3-yl)-amine, tert-butyl-[5-(2,3-dichloro-phenyl)-imidazo[1,2-b][1,2,4]
triazol-6-yl]-amine,
tert-butyl-[5-(2,4-dichloro-phenyl)-imidazo[1,2-b][1,2,4]
triazol-6-yl]-amine,
tert-butyl-[5-(2-methoxy-phenyl)-imidazo[1,2-b][1,2,4]
triazol-6-yl]-amine,
tert-butyl-(5-o-tolyl-imidazo[1,2-b]triazol-6-yl)-amine,
tert-butyl-[5-dimethoxy-phenyl)-imidazo[1,2-b][(1,2,4]
triazol-6-yl]-amine,
tert-butyl-[5-fluorophenyl)-imidazo[1,2-b][1,2,4]triazol-
6-yl]-amine,
tert-butyl-(5-naphthalen-1-imidazo[1,2-b][1,2,4]triazol-
6-yl)-amine,
cyclohexyl-(5-naphthalen-1-yl-imidazo[1,2-b][1,2,4]
triazol-6-yl)-amine,
[5-(2-bromophenyl)-imidazo[1,2-b][1,2,4]triazol-6-yl]-
(1,1,3,3-tetramethyl-butyl)-amine,
N-[4-(6-cyclohexylamino-imidazo[1,2-b][1,2,4]triazol-
5yl)-phenyl)-acetamide,
tert-butyl-[5-(2,5-dimethyl-phenyl)-imidazo[1,2-b][1,2,
4]triazol-6-yl]-amine,
[5-(2,4-dimethyl-phenyl)-imidazo[1,2-b][1,2,4]triazol-
6yl]-(1,1,3,3-tetramethyl-butyl)-amine,
[5-(2,5-dimethyl-phenyl)-imidazo[1,2-b][1,2,4]triazol-6-
yl]-(1,1,3,3-tetramethyl-butyl)-amine, and
N-butyl-N-[5-(2-chloro-6-fluorophenyl)-imidazo[1,2-b]
[1,2,4]triazol-6-yl]-acetamide,
or a pharmaceutically acceptable salt thereof.

7. A pharmaceutical composition comprising at least one pharmaceutically active bicyclic imidazo-5-yl-amine according to claim 1, or a pharmaceutically acceptable salt thereof, and a pharmaceutically acceptable excipient.

8. A pharmaceutical composition according to claim 7, wherein at least one bicyclic imidazo-5-yl-amine is selected from the group consisting of
tert-butyl-(5-furan-2-yl-imidazo[1,2-b][1,2,4]triazol-6-
yl)-amine,
tert-butyl-(5-pyridin-2-yl-imidazo[1,2-b][1,2,4]triazol-6-
yl)-amine,
tert-butyl-(5-pyridin-3yl-imidazo[1,2-b][1,2,4]triazol-6-
yl)-amine,
tert-butyl-(5-pyridin-4yl-imidazo[1,2-b][1,2,4]triazol-6-
yl)-amine,
tert-butyl-(5-methyl-imidazo[1,2-b][1,2,4]triazol-6-yl)-
amine,
cyclohexyl-(5-pyridin-2-yl-imidazo[1,2-b][1,2,4]triazol-
6-yl)-amine,
(2,6-dimethyl-phenyl)-(5-furan-2-yl-imidazo[2-b][1,2,4]
triazol-6yl)-amine,
tert-butyl-(2-phenyl-5H-imidazo[1,2-b]pyrazol-3-yl)-
amine,
tert-butyl-[5-(2,3-dichloro-phenyl)-imidazo[1,2-b][1,2,4]
triazol-6-yl]-amine,
tert-butyl-[5-(2,4-dichloro-phenyl)-imidazo[1,2-b][1,2,4]
triazol-6-yl]-amine,
tert-butyl-[5-(2-methoxy-phenyl)-imidazo[1,2-b][1,2,4]
triazol-6-yl]-amine,
tert-butyl-(5-o-tolyl-imidazo[(1,2-b][1,2,4]triazol-6-yl)-
amine,
tert-butyl-[5-(2,3-dimethoxy-phenyl)-imidazo[1,2-b][1,2,
4]triazol-6-yl]-amine,
tert-butyl-[5-(2-fluorophenyl)-imidazo[1,2-b][1,2,4]
triazol-6-yl]-amine,
tert-butyl-(5-naphthalen-1yl-imidazo[1,2-b][1,2,4]
triazol-6-yl)-amine,
cyclohexyl-(5naphthalen-1-yl-imidazo[1,2-b][1,2,4]
triazol-6yl)-amine,
[5-(2-bromophenyl)-imidazo[1,2-b][1,2,4]triazol-6-yl]-
(1,1,3,3-tetramethyl-butyl)-amine,
N-[4-(6-cyclohexylamino-imidazo[1,2-b][1,2,4]triazol-5-
yl)-phenyl)-acetamide,
tert-butyl- [5(2,5-dimethyl-phenyl)-imidazo[1,2-b][1,2,4]
triazol-6-yl]-amine,
[5-(2,4-dimethyl-phenyl)-imidazo[1,2-b][1,2,4]triazol-6-
yl]-(1,1,3,3-tetramethyl-butyl)-amine,
[5-(2,5-dimethyl-phenyl)-imidazo[1,2-b][1,2,4]triazol-6-
yl]-(1,1,3,3-tetramethyl-butyl)-amine, and
N-butyl-N-[5-(2-chloro-6-fluorophenyl)-imidazo[1,2-b]
[1,2,4]triazol-6-yl]-acetamide.

9. A method for the treatment of pain, comprising administering to a patient in need thereof an effective pain-alleviating amount of a pharmaceutical composition according to claim 7.

10. A process for the preparation of a bicyclic imidazo-5-yl-amine of Formula Ia,

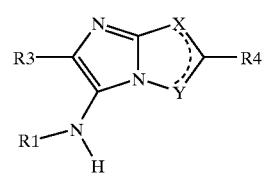

Ia the process being three-component reaction and comprising reacting an amidine of Formula II

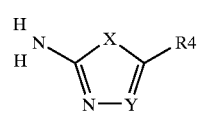

II with an aldehyde of Formula III

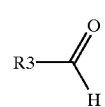

III and an isonitrile of Formula IV

IV in the presence of 20% perchloric acid,
wherein in all formulae,
$R^1$ denotes $C(CH_3)_3$, $(CH_2)_6CN$, optionally substituted phenyl, $C_4$–$C_8$-cycloalkyl, $CH_2CH_2R$ (R=4-morpholino), 1,1,3,3-tetramethylbutyl or $CH_2R^a$, wherein $R^a$ represents hydrogen, branched or unbranched $C_1$–$C_8$-alkyl, optionally substituted phenyl, $CO(OR')$ (where R'=branched or unbranched $C_1$–$C_8$-alkyl), $PO(OR'')_2$ (where R''=branched or unbranched $C_1$–$C_4$-alkyl) or $Si(R^x R^y R^z)$ (where $R^x$, $R^y$ and $R^z$ in each case independently of one another are branched or unbranched $C_1$–$C_8$-alkyl, $C_4$–$C_8$-cycloalkyl or phenyl), $R^3$ denotes branched or unbranched $C_1$–$C_8$-alkyl, $C_3$–$C_8$-cycloalkyl, optionally substituted phenyl, optionally substituted 1-naphthyl, 2naphthyl, quinoline, anthracene, phenanthrene, benzothiophene, benzofurfuryl, optionally substituted pyrrole, 2-pyridyl, 3-pyridyl, 4-pyridyl, optionally substituted furfuryl or optionally substituted thiophene, X denotes $CR^5$ or N, Y is N, $R^4$ and $R^5$ independently of one another denote hydrogen; branched or unbranched $C_1$–$C_8$-alkyl; fluorine; chlorine; bromine; $CF_3$; CN; $NO_2$, $NHR^f$, wherein $R^f$ represents hydrogen, branched or unbranched $C_1$–$C_8$-alkyl or optionally substituted phenyl; $SR^g$, wherein $R^g$ represents hydrogen, branched or unbranched $C_1$–$C_8$-alkyl, phenyl, pyridine, benzyl or fluorenyl; $OR^h$, wherein $R^h$ represents branched or unbranched $C_1$–$C_8$-alkyl, optionally substituted phenyl or CO(OR') (R'= branched or unbranched $C_1$–$C_{8\text{-}alkyl}$; CO(OR') or $CH_2$CO(OR'), wherein R' in each case has the abovementioned meaning or in the case of the group $CH_2$CO(OR') also denotes hydrogen, or an optionally substituted phenyl group, wherein optionally substituted phenyl, optionally substituted 1-naphthyl, optionally substituted pyrrole, optionally substituted furfuryl, optionally substituted thiophene, and optionally substituted alkyl is optionally substituted by one or more substituents selected from the group consisting of a halogen atom, cyano group, nitro group, carboxyl group, hydroxyl group, $C_1$–$C_4$ alkylamido group, $C_1$–$C_4$ alkylamino group, pyrrolidino group, branched or unbranched $C_1$–$C_6$ alkyl group, $C_1$–$C_4$ alkyl group substituted with one or more halogen atoms, $C_1$–$C_4$ alkoxy group, $C_1$–$C_4$ alkoxy group substituted with one or more halogen atoms, and halogen substituted phenoxy group, excluding compounds wherein $R^1$ denotes $C(CH_3)_3$, $R^3$ denotes unsubstituted phenyl, and Y denotes N, or wherein $R^1$ denotes $C(CH_3)_3$, $R^3$ denotes unsubstituted phenyl, Y denotes NH, and X denotes N or $CR^5$, where $R^5$=$CO_2$ethyl.

11. A process according to claim 10, wherein the reaction is carried out in methylene chloride at a temperature of 0° C. to 40° C.

12. A process according to claim 11, wherein the temperature is between 10° C. and 20° C.

13. A process according to claim 11, wherein the compound of Formula II is selected from the group consisting of 3-aminopyrazole, 3-amino-1,2,4-triazole, 2-amino-1,3,4-thiadiazole and 2-aminothiazole.

14. A process for the preparation of a bicyclic imidazo5-yl-amine of Formula I

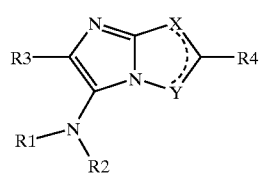

I the process comprising reacting a compound of Formula Ia

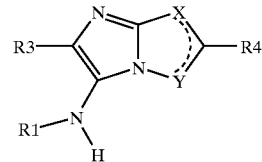

Ia wherein $R^1$ denote $C(CH_3)_3$, $(CH_2)_6CN$, optionally substituted phenyl $C_4$–$C_8$-cycloalkyl, $CH_2CH_2R$ (R=4-morpholino), 1,1,3,3-tetramethylbutyl or $CH_2R^8$, wherein $R^a$ represents hydrogen, branched or unbranched $C_1$–$C_8$-alkyl, optionally substituted phenyl, CO(OR') (where R'=branched or unbranched $C_1$–$C_8$-alkyl), PO(OR")$_2$ (where R"=branched or unbranched $C_1$–$C_4$-alkyl or $Si(R^xR^yR^z)$ (where $R^x$, $R^y$ and $R^z$ in each case independently of one another are branched or unbranched $C_1$–$C_8$-alkyl, $C_4$–$C_8$-cycloalkyl or phenyl), $R^3$ denotes branched or unbranched $C_1$–$C_8$-alkyl $C_3$–$C_8$-cycloalkyl, optionally substituted phenyl, optionally substituted 1-naphthyl, 2-naphthyl, quinoline, anthracene, phenanthrene, benzothiophene, benzofurfuryl, optionally substituted pyrrole, 2-pyridyl, 3-pyridyl, 4-optionally substituted furfuryl or optionally substituted thiophene, X denotes $CR^5$ or N, Y is N, $R^4$ and $R^5$ independently of one another denote hydrogen; branched or unbranched $C_1$–$C_8$-alkyl; fluorine; chlorine; bromine; $CF_3$; CN; $NO_2$ $NHR^f$, wherein $R^f$ represents hydrogen, branched or unbranched $C_1$–$C_8$-alkyl or optionally substituted phenyl; $SR^g$, wherein $R^g$ represents hydrogen, branched or unbranched $C_1$–$C_8$-alkyl phenyl, pyridine, benzyl or fluorenyl; $OR^h$, wherein $R^h$ represents branched or unbranched $C_1$–$C_8$-alkyl, optionally substituted phenyl or CO(OR') (R'=branched or unbranched $C_1$–$C_8$-alkyl; CO(OR') or $CH_2$CO(OR') wherein R' in each case has the abovementioned, meaning or in the case of the group $CH_2$ CO(OR') also denotes hydrogen, or an optionally substituted phenyl group, wherein optionally substituted phenyl optionally substituted 1-naphthyl, optionally substituted pyrrole, optionally substituted furfuryl, optionally substituted thiophene, and optionally substituted alkyl is optionally substituted by one or more substituents selected from the group consisting of a halogen atom, cyano group, nitro group, carboxyl group, hydroxyl group, $C_1$–$C_4$alkylamido group, $C_1$–$C_4$ alkylamino group, pyrrolidino group, branched or unbranched $C_1$–$C_6$ alkyl group, $C_1$–$C_4$ alkyl group substituted with one or more halogen atoms, $C_1$–$C_4$ alkoxy group, $C_1$–$C_4$ alkoxy group substituted with one or more halogen atoms, and halogen substituted phenoxy group, with a compound $R^2$Hal, wherein Hal represents bromine, iodine or chlorine, or with an optionally substituted isocyanate $R^E$NCO in the presence of a morpholine resin in methylene chloride for 2 to 24 hours at a temperature between 10° C. and 40° C., wherein $R^2$ denotes hydrogen; $COR^b$, wherein $R^b$ represents hydrogen, branched or unbranched $C_1$–$C_8$-alkyl, $C_3$–$C_8$-cycloalkyl, $CH_2CH_2CO(OR')$ (where R'=branched or unbranched $C_1$–$C_8$-alkyl), adamantyl, optionally substituted phenyl, optionally substituted 1-naphthyl, 2-naphthyl, 2-pyridyl, 3-pyridyl, 4-pyridyl, thiazolyl or furoyl; $CH_2R^c$, wherein $R^c$ represents hydrogen, branched or unbranched $C_1$–$C_8$-alkyl or optionally substituted phenyl; $CH_2CH_2R^d$, wherein $R^d$ represents optionally substituted phenyl; of $CONHR^E$, wherein $R^E$ represents phenyl, and wherein optionally substituted isocyanate is optionally substituted by one or more substituents selected from the group consisting of a halogen atom, cyano group, nitro group, carboxyl group, hydroxyl group, $C_1$–$C_4$ alkylamido group, $C_1$–$C_4$ alkylamino group, pyrrolidino group, branched or unbranched $C_1$–$C_4$ alkyl group, $C_1$–$C_4$ alkyl group substituted with one or more halogen atoms, $C_1$–$C_4$ alkoxy group, $C_1$–$C_4$ alkoxy group substituted with one or more halogen atoms, and halogen substituted phenoxy group.

15. The process of claim 14, wherein after the reaction excess reagents are removed by filtration through a layer of polymer-bonded tris(2-aminoethyl) amine.

16. The process of claim 14, wherein the compound of Formula Ia is first dissolved in methylene chloride or THF.

17. The process according to claim 14, wherein $R^2Hal$ is an optionally substituted alkyl chloride, aryl chloride or hydrogen chloride.

18. The process of claim 14, wherein the morpholine resin is a polystyrene-morpholine resin.

* * * * *